(12) United States Patent
Bialkowski et al.

(10) Patent No.: US 10,827,996 B2
(45) Date of Patent: Nov. 10, 2020

(54) METHOD FOR OPERATING AN X-RAY DEVICE, X-RAY DEVICE, COMPUTER PROGRAM, AND ELECTRONICALLY READABLE DATA CARRIER

(71) Applicants: Jens Bialkowski, Neunkirchen am Brand (DE); Stephan Lederer, Hallerndorf (DE); Stefan Schneider, Erlangen (DE)

(72) Inventors: Jens Bialkowski, Neunkirchen am Brand (DE); Stephan Lederer, Hallerndorf (DE); Stefan Schneider, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/575,831

(22) Filed: Sep. 19, 2019

(65) Prior Publication Data
US 2020/0085400 A1 Mar. 19, 2020

(30) Foreign Application Priority Data
Sep. 19, 2018 (DE) .................... 10 2018 215 929

(51) Int. Cl.
*A61B 6/02* (2006.01)
*A61B 6/00* (2006.01)

(52) U.S. Cl.
CPC ............... *A61B 6/487* (2013.01); *A61B 6/02* (2013.01); *A61B 6/4233* (2013.01); *A61B 6/541* (2013.01); *A61B 6/4441* (2013.01)

(58) Field of Classification Search
None
See application file for complete search history.

(56) References Cited

U.S. PATENT DOCUMENTS

| 5,967,981 | A | * | 10/1999 | Watrous | ............... | A61B 5/0456 600/428 |
|---|---|---|---|---|---|---|
| 6,904,124 | B2 | * | 6/2005 | Staver | .................... | G01N 23/04 378/62 |
| 7,496,175 | B2 | * | 2/2009 | Sakaguchi | ........... | A61B 6/4233 378/95 |
| 2003/0040820 | A1 | * | 2/2003 | Staver | .................... | G01N 23/04 700/86 |
| 2008/0107233 | A1 | * | 5/2008 | Sakaguchi | ........... | A61B 6/4233 378/91 |
| 2020/0085400 | A1 | * | 3/2020 | Bialkowski | ............... | G01T 1/17 |

* cited by examiner

*Primary Examiner* — Thomas R Artman
(74) *Attorney, Agent, or Firm* — Lempia Summerfield Katz LLC

(57) ABSTRACT

An X-ray device has an X-ray detector allocated to an X-ray tube assembly and configured as a flat panel detector, in which charges, accumulated over an integration period, of individual detector pixels are read out in a readout period following on from the integration period. In order to acquire the X-ray images, a trigger signal is captured, and if a trigger condition evaluating the trigger signal is satisfied, the acquisition of one of the X-ray images takes place using an integration period with a predetermined default length that is the same for all X-ray images. During the acquisition of the time series, in addition to the trigger condition, a readout condition that describes the anticipated imminence of the satisfaction of the trigger condition within a default period that is greater than or equal to the predetermined default length and evaluates the trigger signal is also monitored.

12 Claims, 3 Drawing Sheets

METHOD FOR OPERATING AN X-RAY DEVICE, X-RAY DEVICE, COMPUTER PROGRAM, AND ELECTRONICALLY READABLE DATA CARRIER

This application claims the benefit of DE 10 2018 215 929.7, filed on Sep. 19, 2018, which is hereby incorporated by reference in its entirety.

BACKGROUND

The present embodiments relate to operating an X-ray device during the acquisition of a time series of X-ray images.

In modern imaging (e.g., medical X-ray imaging), digital imaging methods are increasingly being used. In this context, use is not made of an X-ray film or the like, as was originally conventional, but rather, X-ray detectors suitable for taking digital X-rays are used. With X-ray detectors suitable for taking digital X-rays, the X-ray radiation directly or indirectly generates electrical charges that are collected during an integration period in an integration element (e.g., a capacitor), and subsequently read out in a readout period, such that the corresponding accumulated electrical charges are able to be allocated to the individual detector pixels. X-ray detectors of this kind are referred to as flat panel detectors or solid-state detectors. Since these X-ray detectors are not able to measure during the readout period, care should be taken that the readout period of the X-ray pulse lies within the integration period.

For example, in examination procedures for patients, imaging techniques have become known in which a time series of X-ray images is acquired. This provides that a plurality of X-ray images are recorded, distributed over an acquisition period. For this purpose, fluoroscopy sequences are known, for example, in which X-ray images are generated with a constant acquisition frequency. X-ray image chains may be optimized for acquiring individual X-ray images or such time series with constant frequency.

It is also possible, however, for acquisition conditions to exist in which sampling takes place with irregular timing. In this context, it is therefore possible for the temporal spacing between the acquisition of X-ray images in a time series to vary. Usually, the acquisitions of the X-ray images then take place in a triggered manner, where a temporally variable trigger signal is evaluated for the satisfaction of a trigger condition. Examples of acquisition procedures with irregularly timed sampling include, for example, 3D scans, where the acquisition of individual projection images as X-ray images is dependent upon the position of the acquisition arrangement (e.g., the projection angle) or acquisition procedures that are to be triggered by the respiration and/or the heartbeat of a patient. The trigger signal in the first cited example may then, for example, be a position signal that is generated within the X-ray device itself; in the case of biometric signals of a patient to be examined, it is possible, for example, for ECG signals and/or respiratory signals to be used as trigger signal.

For artifact-free image generation, a constant, predefined length of the integration period of the X-ray detector (e.g., the default length in the following) is necessary. As already mentioned, the X-ray pulse is to lie entirely within the integration period. On the other hand, if X-ray detectors are connected and therefore on standby, it is also possible for charges to accumulate outside of X-ray pulses. It is therefore known in the prior art to operate X-ray detectors at a predefined detector cycle, such that integration periods with the default length take place periodically in sequence, separated by readout periods. In this manner, a constant length of the integration periods is provided, and the accumulation of charges outside of imaging procedures is avoided by reading out and discarding the data of unexposed images. With an unfavorable trigger time, however, this leads to difficulties if, for example, X-ray pulses may not be output entirely within an integration period, and the like.

In order to solve the existing problems here, various approaches have been proposed. Thus, it is known in a first solution approach to vary the length of the integration period as a function of the trigger signal. This approach causes interfering artifacts in the X-ray image, but achieves good precision in relation to the constraints to be satisfied, which are described by the trigger condition. In another approach, it has been proposed to vary the trigger time, with the default length of the integration periods remaining constant, so that the trigger time fits into the time pattern of the detector cycle. In this way, the image artifacts are prevented, but the precision in relation to the constraints is impaired.

X-ray detectors that do not generate integration-time-dependent artifacts (e.g., image amplifiers) may be used. These, however, have other disadvantages, such as, for example, geometric image distortions or high costs.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the best possible satisfaction of the constraints described by the trigger condition during irregularly timed acquisition of X-ray images, while maintaining a constant length of the integration period for the X-ray images is enabled.

In accordance with an embodiment, during acquisition of a time series, in addition to a trigger condition, a readout condition that describes anticipated imminence of the satisfaction of the trigger condition within a default period that is greater than or equal to the default length is monitored. The trigger condition evaluates the trigger signal. When the readout condition is satisfied, the X-ray detector is reset by termination of a current integration period, and an integration period with the default length is started. When the trigger condition is satisfied, the X-ray tube assembly is actuated to emit an X-ray pulse immediately within the started integration period, and the X-ray image is read out at the end of the started integration period.

According to one or more of the present embodiments, the temporally variable trigger signal is evaluated to a further extent than only by the trigger condition, since trigger signals used as part of the acquisition of such time series of triggered X-ray images usually have a characteristic course, from which the future occurrence of the trigger condition within a default period may be predicted with a high level of reliability. An additional condition, the readout condition, is therefore used. This provides that shortly before reaching the trigger condition, a current integration period that is irrelevant as far as temporal length is concerned is terminated, and for this, an integration period with the default length, within which it is possible to immediately output the X-ray pulse for the acquisition of the X-ray image when the trigger condition has been satisfied, is provided. In other words, the X-ray detector is reset shortly before the trigger condition is reached based on an evaluation of the trigger signal and is subsequently read out while maintaining the fixed, predetermined integration duration (e.g., the default length). Within the started integration period with the default length, the X-ray pulse may be generated in accordance with the external constraints, described by the trigger condition, with the most exact timing possible (e.g., immediately once the trigger condition has been satisfied within the started integration period). In this context, the resetting of the detector may take place, depending on the embodiment variant of the detector, for example, in that the detector is read out and the associated image is discarded, or in that the running integration period is terminated and the detector information integrated up to that point is discarded, without a readout being required for this purpose.

In one embodiment, checking for the trigger condition may only take place once the readout condition has been absolutely satisfied. In one embodiment, when the trigger condition is satisfied without the readout condition previously being satisfied, this satisfaction of the trigger condition may count both as the satisfied readout condition and also as the satisfied trigger condition.

The checking of the readout condition entails considerable advantages in the temporal sequence. A method, in which when the trigger condition is satisfied, the X-ray detector is reset by the termination of a current integration period, and an integration period with the default length is started, may also be provided. The X-ray pulse is emitted immediately after the beginning of the started integration period with the default length, and the X-ray image is read out at the end of the started integration period with the default length. In this case, however, a specified time delay amounting to the duration of the readout period is accepted, which provides that it is not possible to satisfy the constraints exactly, as is possible when using the readout condition.

The approach according to one or more of the present embodiments thus has the advantage that the exact precision of the X-ray pulse according to the trigger and the fixed integration duration of the X-ray detector may be achieved simultaneously for all X-ray images. This provides that the sources of image artifacts may both be avoided. For example, this enables the cost-optimized selection of flat panel detectors as X-ray detectors, as standard components may be used. By resetting the X-ray detector shortly before the occurrence of the constraints described by the trigger condition, the synchronization of X-ray detector, X-ray tube assembly, and trigger signal is achieved within a short period of time.

Via one or more of the present embodiments, competitive advantages arise for the corresponding manufacturer of X-ray devices as a result of optimized image quality for trigger-signal-dependent X-ray acquisitions while simultaneously using favorable X-ray detectors.

In a development, if the trigger condition has not been satisfied within the started integration period up to a remaining duration of the started integration period that falls below the duration of the X-ray pulse, it may be provided that the started integration period is aborted by resetting the X-ray detector, and a new integration period with the default length is started. This provides that if the X-ray pulse may no longer be generated completely within the desired default length (e.g., the remaining time in the initially started integration period is less than the pulse duration required for the X-ray pulse), then the initially started integration period may be aborted by resetting the detector and the integration may be restarted in order to be ready for the trigger condition and the X-ray pulse once more. Accordingly, the X-ray pulse may then be output in the integration period with the default length that has now been restarted. This embodiment is useful if the at least one constraint described by the trigger condition (e.g., a certain respiratory state) occurs later than predicted.

In an embodiment, the reverse case (e.g., that the trigger condition is satisfied very early) may be taken into consideration by the X-ray pulse being output immediately at the beginning of the started integration period if the trigger condition occurs before the end of the readout period preceding the start of the integration period with the default length. If, for example, the satisfaction of the trigger condition thus immediately follows the satisfaction of the readout condition (or, as explained above, both are to be considered as satisfied simultaneously), then the X-ray pulse is generated as soon as possible (e.g., at the beginning of the started integration period with the default length, which may also be understood to be "immediately within the started integration period"). Even if the constraint occurs earlier than expected, it is thus possible to react quickly enough.

In one embodiment, the readout condition may evaluate a course over time (e.g., smoothed) of the trigger signal to predict the satisfaction of the trigger condition. As already mentioned, frequently used trigger signals are substantially steady, so that typical courses (e.g., in smoothed form) that make it possible to predict, in a sufficiently reliable manner by simply consulting the course, the occurrence of the constraints, and consequently, the satisfaction of the trigger condition that also evaluates the trigger signal, are given. For example, respiratory and/or ECG signals are periodic, providing that it is possible to draw certain conclusions. If the trigger signal is, for example, a position signal of a component of the X-ray device (e.g., a C-arm or an X-ray tube assembly), then a certain movement in the form of the acquisition trajectory may be predefined for the component, providing that it is also possible to estimate when certain trigger positions are reached.

As already indicated, it is possible, for example, to use a position signal at least of the X-ray tube assembly along an acquisition trajectory (e.g., a projection angle signal) and/or a biometric signal of a patient to be examined (e.g., an ECG signal and/or a respiratory signal) as the trigger signal. If, for example, an X-ray device with a C-arm, to which the X-ray tube assembly and the X-ray detector are fastened opposite one another, is used, it is possible for a rotation of the C-arm and thus a movement of the X-ray tube assembly along a circular path to be performed for the acquisition of projection images as X-ray images, which are based on the reconstruction of a three-dimensional image data record. Each position along the circular path corresponds to a projection angle. If, at certain projection angles, X-ray images are now acquired, specifically, for example, projection images for reconstruction, then corresponding trigger conditions may be defined for the projection angles. If a movement of the C-arm that is steady on average is assumed, then it is possible to predict very effectively (e.g., with regard to the desired default period) when the next image acquisition position (e.g., the next projection angle at which an X-ray image is to be acquired) is predicted to be reached. The addressed exception handling (e.g., aborting a started integration period and starting a new integration period) or trigger condition already satisfied during the readout period corresponds in this exemplary embodiment to the cases in which the C-arm moves too slowly or too quickly.

Even ECG and/or respiration-triggered acquisitions of X-ray images have already been proposed in the prior art, providing that corresponding ECG signals and/or respiratory signals already find use as trigger signals. For these trigger signals, it holds that the trigger signals have a substantially periodic course that makes it possible to predict (e.g., also while taking into consideration the period duration in the past) in a relatively reliable manner. If, for example, the respiration is still slower than expected for a time, then the exception handling described above may engage in cases of doubt, and a new integration period with the default length may be started.

In some X-ray detectors, too great a charge accumulation may be prevented from occurring, which would provide that an integration period is lasting too long. In the context of the present embodiments, the integration periods between the actual acquisition of X-ray images ultimately have an arbitrary length if no such technical restriction or protective restriction is to be observed. This may also be taken into consideration in the context of the present embodiments, however, in that it is possible to provide, for example, that, beyond the integration periods with the default length, a maximum period length of the integration periods is used. At the end of this, if the readout condition is not satisfied, a resetting of the detector takes place, whereupon a new integration period is started. In the new integration period, it is checked whether the readout condition is satisfied. In this context, a development may be provided that if the readout condition is satisfied due to the maximum period length being reached within the readout period during readout, the integration period with the default length is started immediately after this readout period.

In addition to the method, the present embodiments also relate to an X-ray device. The X-ray device includes an acquisition arrangement with an X-ray detector configured as a flat panel detector, and an X-ray tube assembly. The X-ray device also includes a trigger signal generator and a control device (e.g., a controller or one or more processors) configured to perform a method according to the present embodiments. In this context, the control device may have at least one processor and/or storage device. All the embodiments relating to the method may be transferred analogously to the X-ray device, which therefore likewise entails the aforementioned advantages.

The acquisition arrangement may be arranged on a C-arm of the X-ray device (e.g., the X-ray detector and the X-ray tube assembly at mutually opposite ends of the C-arm). Other embodiments may also be provided, however, with components of the X-ray arrangement that may be moved in an independent and coupled manner. The trigger signal generation device may, with a position signal as part of the trigger signal, be the control device itself, but may also be provided separately. If a biometric signal of a patient is used, then corresponding measuring devices may be used as trigger signal generation devices that provide the trigger signal via an interface of the control device. For example, this may involve a respiratory sensor and/or respiratory belt and/or an ECG measuring device. The control device may also be at least partially integrated in other components of the X-ray device. For example, functional units specifically provided for the method according to the present embodiments may be provided as integrated in the X-ray detector itself.

To perform the method according to one or more of the present embodiments, the control unit may have, in addition to an interface, via which the trigger signal is received, a general control unit for actuating the X-ray detector and the X-ray tube assembly, a first evaluation unit for monitoring the readout condition, and a second evaluation unit for monitoring the trigger condition. The first evaluation unit and the second evaluation unit may be formed by one or more processors.

A computer program according to the present embodiments may be loaded, for example, directly into a memory of a control device of an X-ray device and has program means in order to carry out the acts of a method described herein when the computer program is executed in the control device of the X-ray device. The computer program may be stored on an electronically readable data carrier (e.g., a non-transitory computer-readable storage medium) according to the present embodiments. The electronically readable data carrier therefore includes electronically readable control information (e.g., instructions) stored thereon. The electronically readable control information includes at least one cited computer program and is configured such that, on use of the data carrier in a control device of an X-ray device, the control information carries out a method according to the present embodiments. The data carrier may involve, for example, a non-transient data carrier (e.g., a CD-ROM).

DETAILED DESCRIPTION

Figure 1:
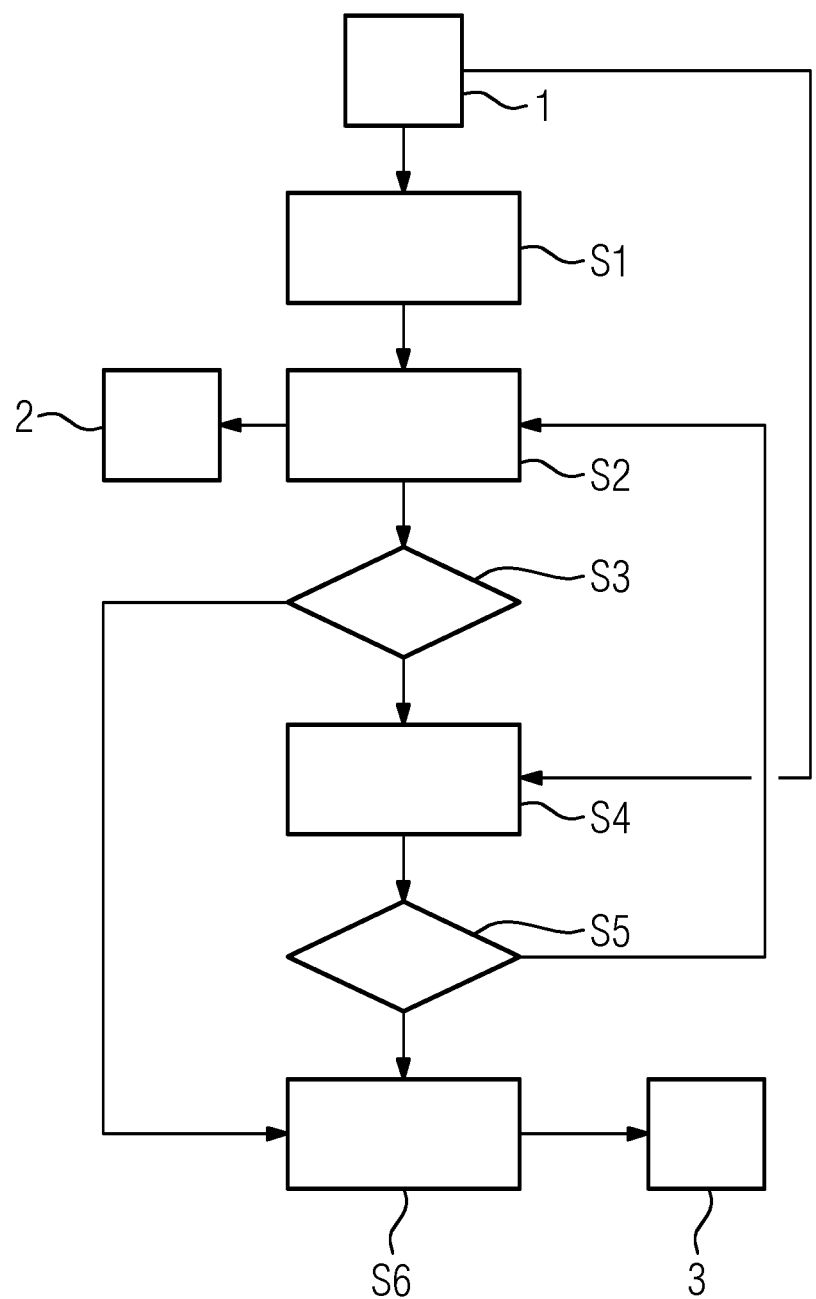
FIG. 1 shows a flow chart of an exemplary embodiment of a method.

FIG. 1 shows a flow chart of an exemplary embodiment of a method. In this context, a time series of X-ray images are to be acquired. Temporal spacings between the acquisition of the individual X-ray images do not necessarily need to be the same, but rather are generally different. In the exemplary embodiment that is specifically addressed below, a projection angle signal of the X-ray device, which has a C-arm on which an X-ray detector, embodied as a flat panel detector, and an X-ray tube assembly are arranged opposite one another, is provided as a trigger signal that is evaluated by a trigger condition for the acquisition of X-ray images, as a type of position signal (e.g., rotational position of the C-arm). At certain, predefined projection angles, the trigger condition is satisfied. In this manner, X-ray images with different projection directions are acquired (e.g., as two-dimensional projection images for reconstructing a three-dimensional image data record).

A trigger signal generation device 1, which may be part of the X-ray device, is shown in FIG. 1 as a source of the trigger signal, which is initially used in act S1, however, to check a readout condition. The readout condition likewise evaluates the trigger signal and checks whether the trigger condition has been satisfied in a default period following the satisfaction. In this context, the length of the default period is chosen as a function of a default length for the integration period to be used for all X-ray images during the acquisition of the X-ray image (e.g., such that when the trigger condition occurs in the default period, the X-ray pulse comes to lie in a readily explained, started integration period with the default length, as a default length plus pulse duration). Since, although the movement speed of the C-arm in the specific exemplary embodiment fluctuates somewhat, but nonetheless may be predicted relatively well, it is possible to check in the readout condition, for example, whether a certain degree value before a projection angle is present, at which an X-ray image is to be acquired, at which the trigger condition is therefore satisfied (e.g., 4° before a projection angle of this kind for the acquisition of a projection angle as X-ray image).

If the readout condition is satisfied in act S1, then in act S2, the current integration period of the X-ray detector is terminated and a resetting of the X-ray detector takes place in a readout period. As described above, for the purpose of resetting the X-ray detector, either a readout takes place and the readout result is discarded as an unexposed X-ray image, or the detector information integrated up to that point is discarded without preceding readout. After this readout period, a new integration period with the default length immediately begins. In act S2, the X-ray detector 2, which is likewise indicated in FIG. 1, is therefore actuated (see the corresponding arrow).

In act S3, a first exception handling is checked (e.g., whether the trigger condition is already satisfied during the readout period of act S2). If this is the case, then there is an immediate jump forward to act S6, in which at the earliest possible time within the started integration period, the X-ray pulse is output for acquisition of the X-ray image (see the shown actuation of the X-ray tube assembly 3), which provides that in the present case, at the beginning of the integration period with the default length, the X-ray pulse is also immediately output. This will not usually be the normal scenario, however, but rather will only occur when the C-arm moves considerably too quickly in the specific exemplary embodiment.

In act S4, after the start of the integration period with the default length, the satisfaction of the trigger condition is then monitored. In turn, as indicated by the corresponding arrow from the trigger signal generation device 1, this evaluates the trigger signal. In this context, however, it is also checked in parallel in act S5 whether the remaining duration of the started integration period would be absolutely sufficient in order to output the X-ray pulse. This, for example, may not be the case if the C-arm is moving too slowly in the specific exemplary embodiment. The method then returns to act S2, which provides that a resetting of the X-ray detector is performed once more and the integration period with the default length is started once more.

When the trigger condition is satisfied in act S4 (and if there is sufficient remaining time for the X-ray pulse in the started integration period), then the method proceeds to act S6, providing that immediately on satisfaction of the trigger condition, the output of the X-ray pulse may also take place. Therefore, ideally, no time loss arises in the normal scenario.

Figure 2:
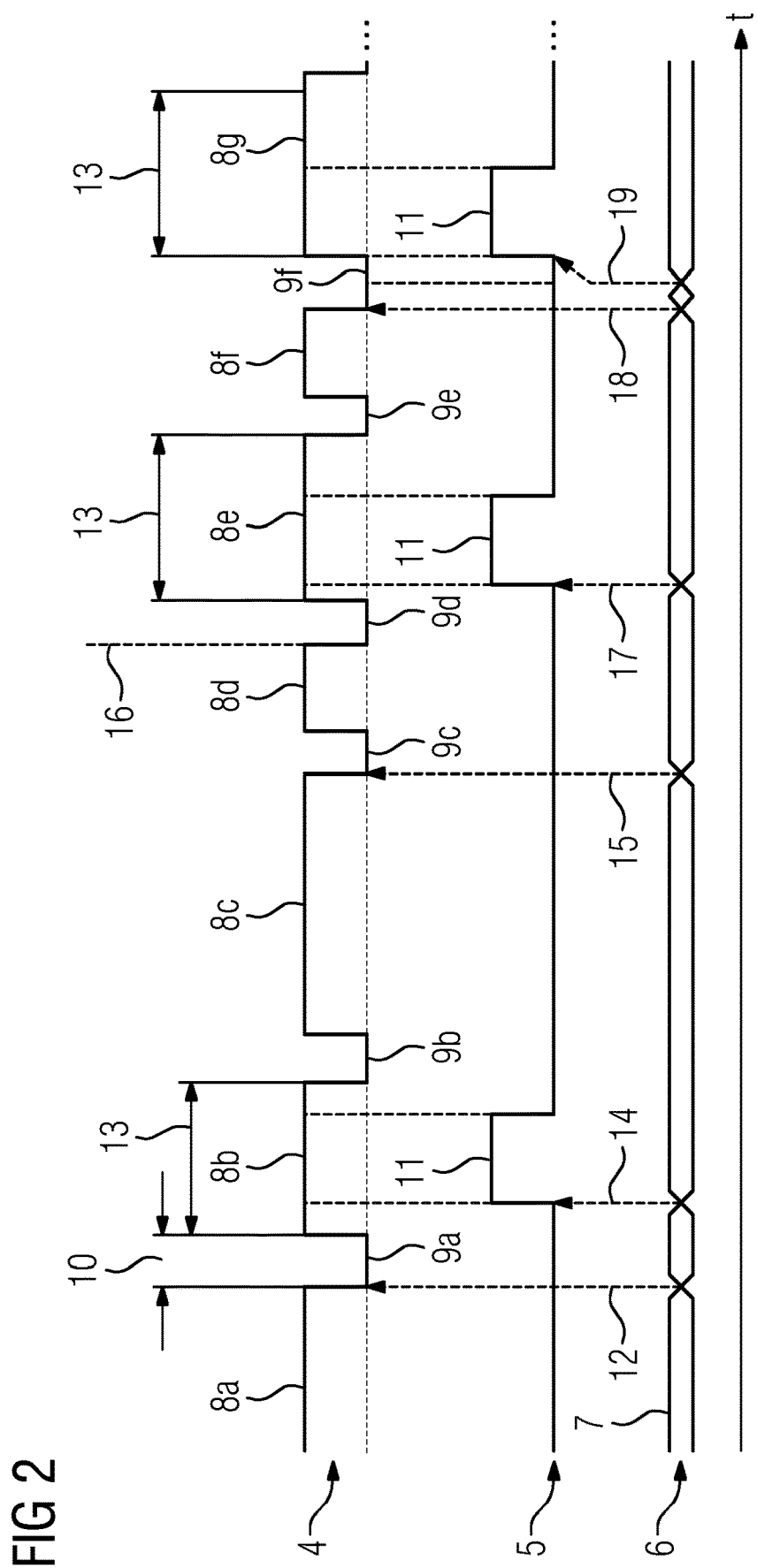
FIG. 2 shows various exemplary signals and periods in course over time.

The time relationships explained in the flow diagram in FIG. 1 are explained again in further detail by the temporal flow chart in FIG. 2. In this context, the upper graph 4 shows the activity of the X-ray detector 2, the central graph 5 shows the activity of the X-ray tube assembly 3, and the lower graph 6 symbolizes the trigger signal 7.

During operation of the X-ray detector 2, integration periods 8a to 8g, in which the X-ray detector 2 is in principle able to accumulate electrical charges on incident radiation in integration elements of individual detector pixels, exist. Between the integration periods 8a to 8g, there are in each case readout periods 9a to 9f, in which the individual detector pixel charges of the X-ray detector 2, as known in principle in the prior art, are read out. In these readout periods 9a to 9f, it is not possible for X-ray data to be acquired using the X-ray detector 2. The readout periods 9a to 9f have a constant readout length 10 (e.g., readout time duration). This does not apply to the integration periods 8a to 8g, as is demonstrated in further detail below.

In relation to the operation of the X-ray tube assembly 3, there is provision for a plurality of X-ray pulses 11 with a fixed pulse length, which may be seen.

The trigger signal 7, which in the reality of the specific exemplary embodiment corresponds to a monotonically increasing projection angle, for the purpose of an improved explanation, is represented in FIG. 2 such that certain times with certain projection angles are highlighted by nodes.

Thus, for example, a projection angle of 16° is reached at time 12. This lies 4° before the projection angle of 20°, at which an X-ray image is to be acquired. This provides that the readout condition is satisfied at time 12, so that according to the case shown there, the X-ray detector 2 is actuated to terminate the integration period 8a and to begin the readout period 9a, which connects to the beginning of the integration period 8b, which should have the default length 13.

At time 14, the projection angle of 20° is indicated in the trigger signal, which provides that the trigger condition is satisfied. The X-ray pulse 11 to be generated may thus be completely output within the started integration period 8b, providing that the X-ray tube assembly 3 is actuated accordingly. After the end of the default length of the integration period 8b, the X-ray image is read out in the readout period 9b. This constellation shown represents the normal scenario. Connecting to the readout period 9b is the integration period 8c with a length not initially specified (e.g., arbitrary).

At time 15, the projection angle of 36° is reached, which is 4° removed from the projection angle 40°, at which an X-ray image is to be acquired. The readout condition is thus satisfied, and the integration period 8c is aborted in favor of the readout period 9c. The integration period 8d is then started with the aim of extending the period over the default length. It is specified at time 16, however, that it would now no longer be possible for the X-ray pulse 11 to be output completely within the integration period 8d if the period were to have the default length, but that no trigger condition has also occurred. For this reason, at time 16, the integration period 8d is aborted, and in turn, a reset takes place in the readout period 9d. A new integration period 8e set with the default length 13 is thus begun. At time 17, according to trigger signal 7, the projection angle of 40° is finally reached (e.g., the C-arm has moved slowly), so that accordingly, the X-ray tube assembly 3 is immediately actuated to output the X-ray pulse 11. As shown, the X-ray pulse 11 may lie completely within the integration period 8d. In readout period 9e, the corresponding X-ray image for the projection angle 40° is then read out.

An integration period 8f with ultimately any arbitrary length now follows. This time is particularly short, since at time 18, the projection angle of 56° has already been reached, the readout condition is satisfied, and the integration period 8f is aborted in favor of the readout period 9f. In the special case illustrated by this, the C-arm moves more quickly than expected, since the projection angle of 60° is already reached at time 19. Therefore, the trigger condition is satisfied. In such a case, at the beginning of the integration period 8g with the default length 13, the X-ray pulse 11 is also immediately output.

Even if a specific exemplary embodiment for the rotation of a C-arm has been described in the present case, the concepts described here may also be transferred to other trigger signals (e.g., biometric trigger signals such as ECG signals and/or respiratory signals).

For the integration periods 8a, 8c and 8f, in which there is a wait for the satisfaction of the readout condition, it is possible for maximum period lengths to be provided, at the end of which the readout takes place. There follows a new intermediate integration period 8. If the readout conditions are satisfied within this readout period 9, it is also possible for one of the integration periods 8 with the default length 13 to be started next, immediately after the readout period.

Figure 3:
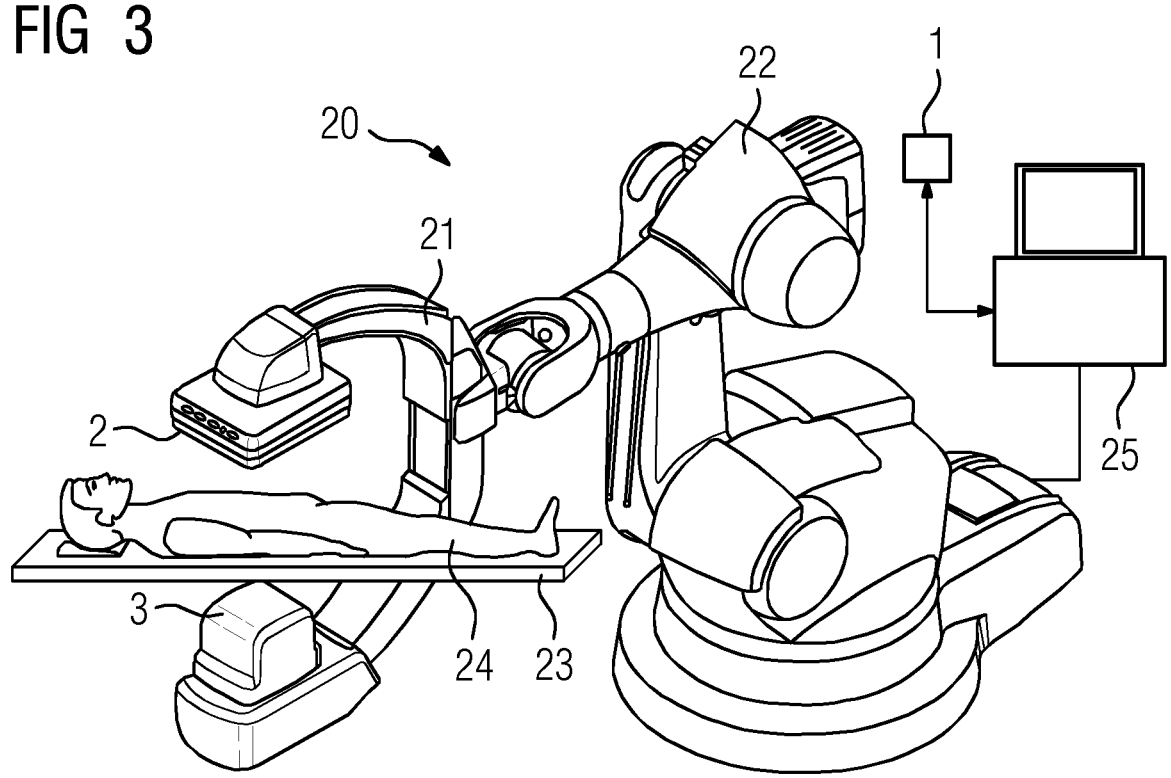
FIG. 3 shows one embodiment of an X-ray device.

FIG. 3 shows a schematic view of an X-ray device 20 according to an embodiment. The X-ray device 20 includes a C-arm 21, on which an X-ray detector 2 and an X-ray tube assembly 3 are arranged opposite one another. Using a robot arm 22, the C-arm 21 may be placed in various acquisition geometries in relation to a patient 24 supported on a patient couch 23.

The operation of the X-ray device 20 is controlled by a control device 25 that is configured for performing the method according to one or more oft he present embodiments. The control device 25 may, for example, communicate with a trigger signal generation device 1 that may also be implemented as part of the control device 25 if, for example, a position signal of the X-ray tube assembly 3 along the acquisition trajectory is used as trigger signal 7. As an alternative or in addition, the trigger signal generation deice 1 (e.g., when measuring biometric signals as trigger signals 7) may be arranged on the patient 24 (e.g., as an ECG device and/or respiratory sensor).

Figure 4:
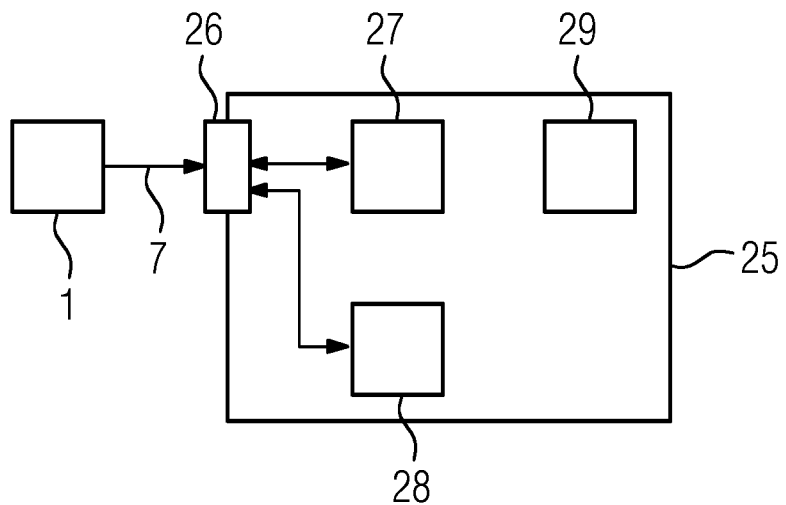
FIG. 4 schematically shows exemplary functional units in a control device of the X-ray device.

FIG. 4 shows a schematic sketch of possible functional units of the control device 25 with regard to the present embodiments. The control device 25 has an interface 26 for receiving the triggering signal 7. A first evaluation unit 27 evaluates the trigger signal 7 with regard to the readout condition, and a second evaluation unit 28 evaluates the trigger signal 7 with regard to the trigger condition. Further functional units may include, for example, a general control unit 29 for higher-level control and/or actuation of the X-ray tube assembly 3/X-ray detector 2, and also other components.

Although the invention has been illustrated and described in detail using the exemplary embodiment, the invention is not limited by the disclosed examples, and a person skilled in the art may derive other variations therefrom without departing from the scope of protection of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating an X-ray device during acquisition of a time series of X-ray images, wherein the X-ray device has an X-ray detector allocated to an X-ray tube assembly and configured as a flat panel detector, in which charges, accumulated over an integration period, of individual detector pixels are read out in a readout period following on from the integration period, wherein in order to acquire the X-ray images, a trigger signal is captured, and if a trigger condition evaluating the trigger signal is satisfied, the acquisition of one of the X-ray images takes place using an integration period with a predetermined default length, which is the same for all of the X-ray images, the method comprising:
   monitoring, during the acquisition of the time series, in addition to the trigger condition, a readout condition that describes an anticipated imminence of the satisfaction of the trigger condition within a default period that is greater than or equal to the predetermined default length, and evaluates the trigger signal;
   when the readout condition is satisfied:
      resetting the X-ray detector, the resetting comprising terminating a current integration period; and
      starting an integration period with the predetermined default length; and
   when the trigger condition is satisfied:
      actuating the X-ray tube assembly, such that an X-ray pulse is emitted immediately within the started integration period; and
      reading out the X-ray image at an end of the started integration period.

2. The method of claim 1, further comprising:
   aborting the started integration period when the trigger condition has not been satisfied within the started integration period up to a remaining duration of the started integration period that falls below the duration of the X-ray pulse, the aborting comprising resetting the X-ray detector; and
   starting a new integration period with the predetermined default length.

3. The method of claim 1, further comprising outputting the X-ray pulse immediately at a beginning of the started integration period when the trigger condition occurs before an end of the readout period preceding a start of the integration period with the predetermined default length.

4. The method of claim 1, wherein the readout condition evaluates a course over time of the trigger signal, such that the satisfaction of the trigger condition is predicted.

5. The method of claim 4, wherein the course is a smoothed course.

6. The method of claim 1, wherein a position signal at least of the X-ray tube assembly along an acquisition trajectory, a biometric signal of a patient to be examined, or the position signal and the biometric signal are used as the trigger signal.

7. The method of claim 6, wherein the position signal is a projection angle signal.

8. The method of claim 6, wherein the biometric signal is an ECG signal, a respiratory signal, or the ECG signal and the respiratory signal.

9. The method of claim 1, wherein beyond the integration periods with the predetermined default length, a maximum period length of the integration periods is used, and
   wherein the method further comprises:
      resetting the X-ray detector at the end of the maximum period length when the readout condition is not satisfied; and
      starting a new integration period and checking whether the readout condition is satisfied during the new integration period.

10. The method of claim 9, further comprising when the readout condition is satisfied due to the maximum period length being reached within the readout period during readout, immediately starting the integration period with the predetermined default length after the readout period.

11. An X-ray device comprising:
an acquisition arrangement including an X-ray detector configured as a flat panel detector, and an X-ray tube assembly, wherein the flat panel detector is configured to read out charges, accumulated over an integration period, of individual detector pixels in a readout period following on from an integration period;
a trigger signal generator; and
a controller configured to operate the X-ray device during acquisition of a time series of X-ray images, wherein in order to acquire the X-ray images, a trigger signal is captured, and when a trigger condition evaluating the trigger signal is satisfied, the acquisition of one of the X-ray images takes place using the integration period with a predetermined default length, which is the same for all of the X-ray images, the method operation of the X-ray device comprising:
 monitor, during the acquisition of the time series, in addition to the trigger condition, of a readout condition that describes an anticipated imminence of the satisfaction of the trigger condition within a default period that is greater than or equal to the predetermined default length, and evaluation of the trigger signal;
 when the readout condition is satisfied:
  reset of the X-ray detector, the reset comprising termination of a current integration period; and
  start of an integration period with the default length; and
 when the trigger condition is satisfied:
  actuation of the X-ray tube assembly, such that an X-ray pulse is emitted immediately within the started integration period; and
  read out of the X-ray image at the end of the started integration period.

12. In a non-transitory computer readable storage medium that stores instructions executable by one or more processors to operate an X-ray device during acquisition of a time series of X-ray images, wherein the X-ray device has an X-ray detector allocated to an X-ray tube assembly and configured as a flat panel detector, in which charges, accumulated over an integration period, of individual detector pixels are read out in a readout period following on from the integration period, wherein in order to acquire the X-ray images, a trigger signal is captured, and if a trigger condition evaluating the trigger signal is satisfied, the acquisition of one of the X-ray images takes place using an integration period with a predetermined default length, which is the same for all of the X-ray images, the instructions comprising:
 monitoring, during the acquisition of the time series, in addition to the trigger condition, a readout condition that describes an anticipated imminence of the satisfaction of the trigger condition within a default period that is greater than or equal to the predetermined default length, and evaluates the trigger signal;
 when the readout condition is satisfied:
  resetting the X-ray detector, the resetting comprising terminating a current integration period; and
  starting an integration period with the predetermined default length; and
 when the trigger condition is satisfied:
  actuating the X-ray tube assembly, such that an X-ray pulse is emitted immediately within the started integration period; and
  reading out the X-ray image at an end of the started integration period.

* * * * *